United States Patent
Enomoto (10) Patent No.: US 8,132,951 B2
(45) Date of Patent: Mar. 13, 2012

(54) ENDOSCOPE SYSTEM

(75) Inventor: Takayuki Enomoto, Saitama (JP)

(73) Assignee: Hoya Corporation, Tokyo (JP)

( * ) Notice: Subject to any disclaimer, the term of this patent is extended or adjusted under 35 U.S.C. 154(b) by 396 days.

(21) Appl. No.: 12/412,463

(22) Filed: Mar. 27, 2009

(65) Prior Publication Data

US 2009/0244924 A1 Oct. 1, 2009

(30) Foreign Application Priority Data

Mar. 31, 2008 (JP) .................................. 2008-092651

(51) Int. Cl.
*A61B 1/06* (2006.01)

(52) U.S. Cl. ........ 362/574; 362/228; 362/234; 362/253; 362/551; 362/572

(58) Field of Classification Search .......... 362/227–228, 362/234, 253, 551, 572, 574
See application file for complete search history.

(56) References Cited

U.S. PATENT DOCUMENTS

| | | |
|---|---|---|
| 6,294,775 B1 | 9/2001 | Seibel et al. |
| 2002/0177861 A1 | 11/2002 | Sugiyama et al. |
| 2005/0215996 A1 | 9/2005 | Ouchi |
| 2007/0149851 A1 | 6/2007 | Nakamura et al. |
| 2007/0282336 A1 | 12/2007 | Kawano |
| 2008/0165360 A1* | 7/2008 | Johnston ........................ 356/394 |
| 2009/0219384 A1* | 9/2009 | Iketani et al. ................... 348/45 |

FOREIGN PATENT DOCUMENTS

| | | |
|---|---|---|
| JP | 9-38093 | 2/1997 |
| JP | 2005-321930 | 11/2005 |
| JP | 2007-307298 | 11/2007 |

OTHER PUBLICATIONS

English language Abstract of JP 2007-307298, Nov. 29, 2007.
English language Abstract of JP 2005-321930, Nov. 17, 2005.
English language Abstract of JP 9-38093, Feb. 10, 1997.

* cited by examiner

*Primary Examiner* — Stephen F Husar
*Assistant Examiner* — Meghan Dunwiddie
(74) *Attorney, Agent, or Firm* — Greenblum & Bernstein, P.L.C.

(57) ABSTRACT

An endoscope system comprises first and second emitters, a fiber, and a controller. The first emitter emits illumination light to a photographic subject. The second emitter emits infrared light. Emission intensity of the second emitter is stronger than that of the first emitter. The fiber has a tip which moves in a spiral when viewed from the photographic subject during scan periods. The controller controls emission timing of the first and second emitters. Light emitted by the first and second emitters is cast from the tip of the fiber onto the photographic subject. The second emitter emits in a predetermined period of one of the scan periods, based on control of the emission timing, so as to shine infrared light with the second emitter to at least one part of the photographic subject, in order to perform marking.

6 Claims, 9 Drawing Sheets

ENDOSCOPE SYSTEM

BACKGROUND OF THE INVENTION

1. Field of the Invention

The present invention relates to an endoscope system that performs a treatment, such as marking, easily and accurately.

2. Description of the Related Art

An endoscope system that performs marking on tissue in the vicinity of an affected region for treating the affected region has previously been proposed.

Examples of marking including an embodiment that injects black writing fluid by needle, and an embodiment that attaches clips, etc., are cited.

Japanese unexamined patent publication (KOKAI) No. H09-38093 discloses a treatment device for the endoscope system that uses tack for marking.

However, in the embodiments mentioned above, it is necessary to use the forceps channel in order to bring the treatment device to the marking position in the vicinity of the affected region. This skill requires practice by the operator.

SUMMARY OF THE INVENTION

Therefore, an object of the present invention is to provide an endoscope system that performs a treatment on an intended position easily and accurately.

According to the present invention, an endoscope system comprises a first emitter, a second emitter, a fiber, and a controller. The first emitter emits at least one of illumination light and excitation light to a photographic subject. The second emitter emits infrared light. Emission intensity of the second emitter is stronger than emission intensity of the first emitter. The fiber has a tip which moves in a spiral when viewed from the photographic subject during scan periods. The controller controls emission timing of the first emitter and the second emitter. Light emitted by the first emitter and the second emitter is cast from the tip of the fiber onto the photographic subject. The second emitter emits in a predetermined period of one of the scan periods, based on control of the emission timing, so as to shine infrared light with the second emitter to at least one part of the photographic subject, in order to perform marking.

BRIEF DESCRIPTION OF THE DRAWINGS

The objects and advantages of the present invention will be better understood from the following description, with reference to the accompanying drawings in which.

DESCRIPTION OF THE PREFERRED EMBODIMENTS

Figure 1:
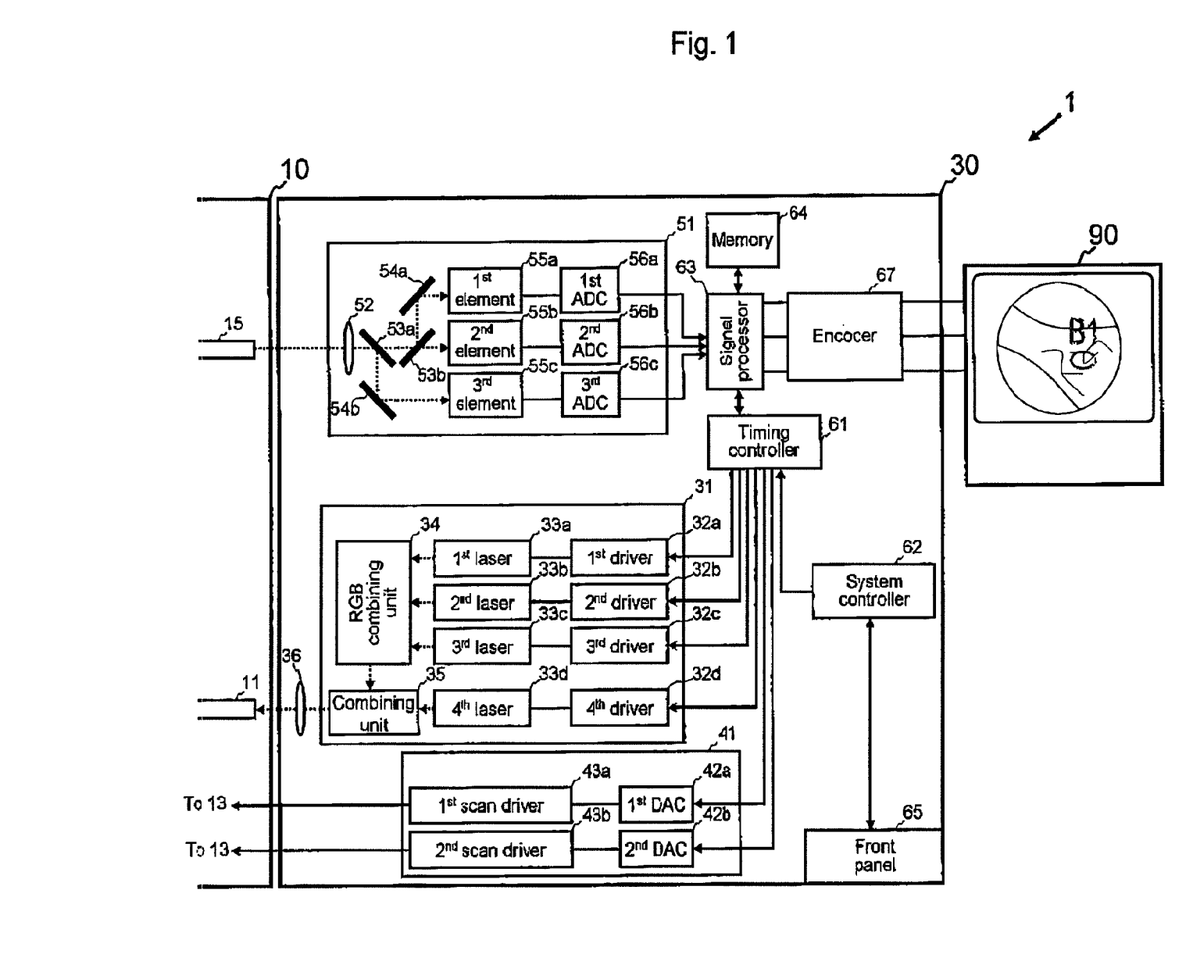
FIG. 1 is a construction diagram of the endoscope system in the embodiment.

The present invention is described below with reference to the embodiments shown in the drawings (FIGS. 1 to 9). As shown in FIG. 1, an endoscope system 1 in the embodiment is a full-color scanning fiber endoscope and comprises a probe 10, a processor 30, and a display 90.

Figure 2:
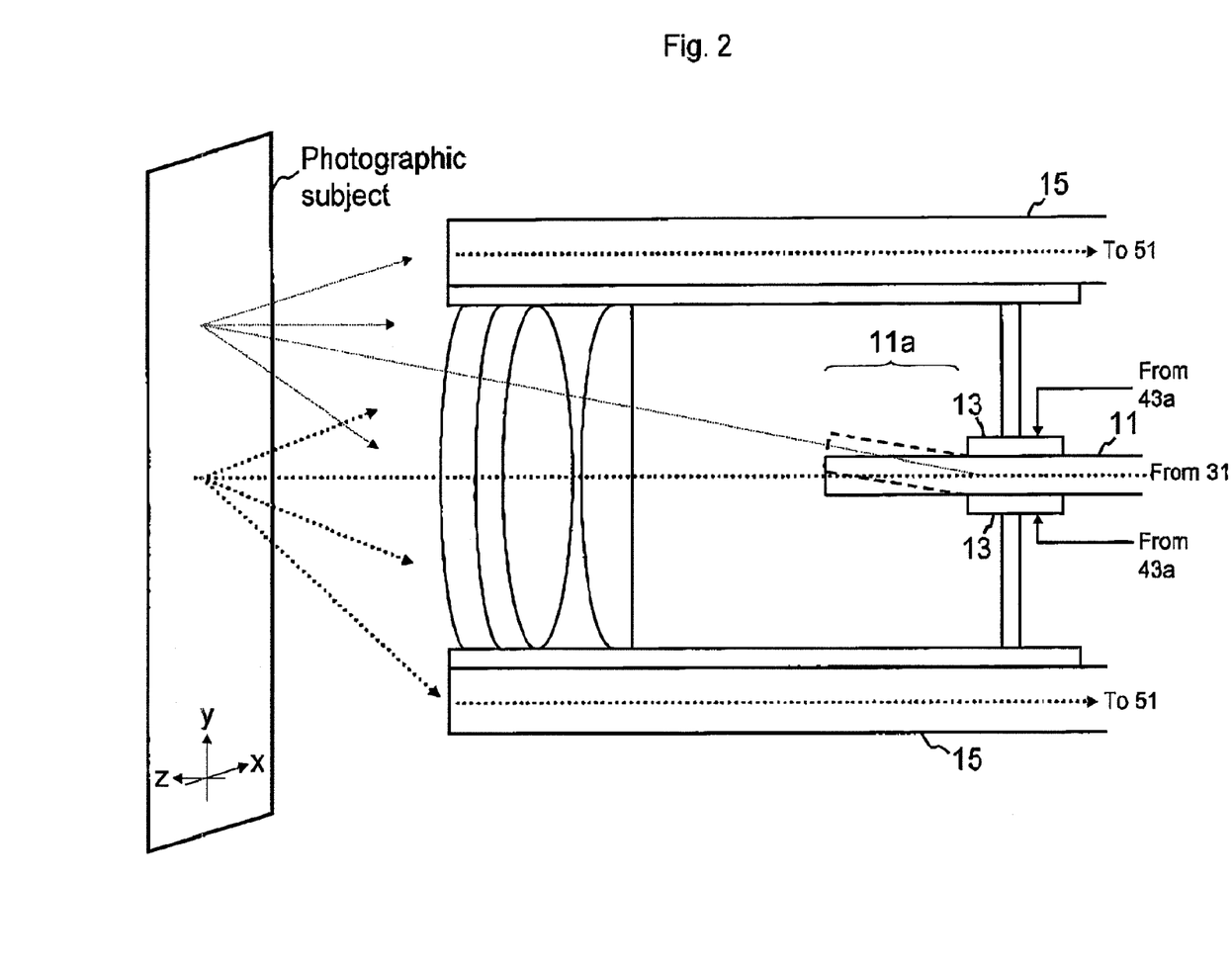
FIG. 2 is a cross-sectional construction diagram of the front tip of the probe.

By way of orientation, in the embodiment, direction x, direction y, and direction z are defined (see FIG. 2). Direction x is the direction perpendicular to the optical axis LX. Direction y is the direction perpendicular to the optical axis LX and direction x. Direction z is the direction parallel to the optical axis LX and perpendicular to both direction x and direction y.

The optical axis LX is the optical axis of an inflexible part of the fiber 11 which is used for illuminating. The inflexible part is not moved or twisted by the scan unit 13, and is arranged at the near side of bendable part of the tip 11a of the fiber 11.

The probe 10 has a fiber 11 for illuminating, a scan unit 13, and fibers 15 for receiving. The fiber 11, which is the scanning fiber, guides light from the light source 31 of the processor 30 to the tip 11a of the fiber 11, and emits light from the tip 11a to the photographic subject which may be the body (tissue) of a patient, etc. Light emitted from the fiber 11 is reflected by the photographic subject and guided to the light sensor 51 of the processor 30 through the fibers 15.

The fibers 15, which are the backscatter return fibers, are arranged around the fiber 11. The scan unit 13 is arranged at the vicinity of the tip 11a of the fiber 11. The scan unit 13 has a piezoelectric device, and oscillates the tip 11a in direction x and in direction y so as to rotate the tip 11a in a spiral when viewed from direction z. The spiral rotation directs the light emitted from the tip 11a of the fiber 11 in a spiral around the optical axis LX as viewed from direction z in so-called spiral track scanning (see the dotted arrow in FIG. 5).

The light reflected from the photographic subject, which is emitted from the fiber 11 and whose emission direction changes in a spiral is guided to the light sensor 51 of the processor 30 through the fibers 15, to form a photographic subject image.

The heavy dotted line in FIG. 2 shows the situation in which white light is emitted from the tip 11a in direction z and then the light reflected by the photographic subject is guided to the light sensor 51 through the fibers 15, in the initial state before the tip 11a is oscillated.

The thin dotted line in FIG. 2 shows the situation in which the bendable part of the tip 11a is twisted so that the tip 11a is moved in direction y and upward from the initial state, and white light is emitted from the tip 11a in the direction that the emission surface of the tip 11a is facing, and then the white light reflects off of the photographic subject.

During a scan period of the field period, the direction of the light emitted from the tip 11a of the fiber 11 changes in a spiral around the optical axis LX as viewed from direction z, and the first, second, and third lasers 33a, 33b, and 33c of the light source 31 emit continuously.

Figure 5:
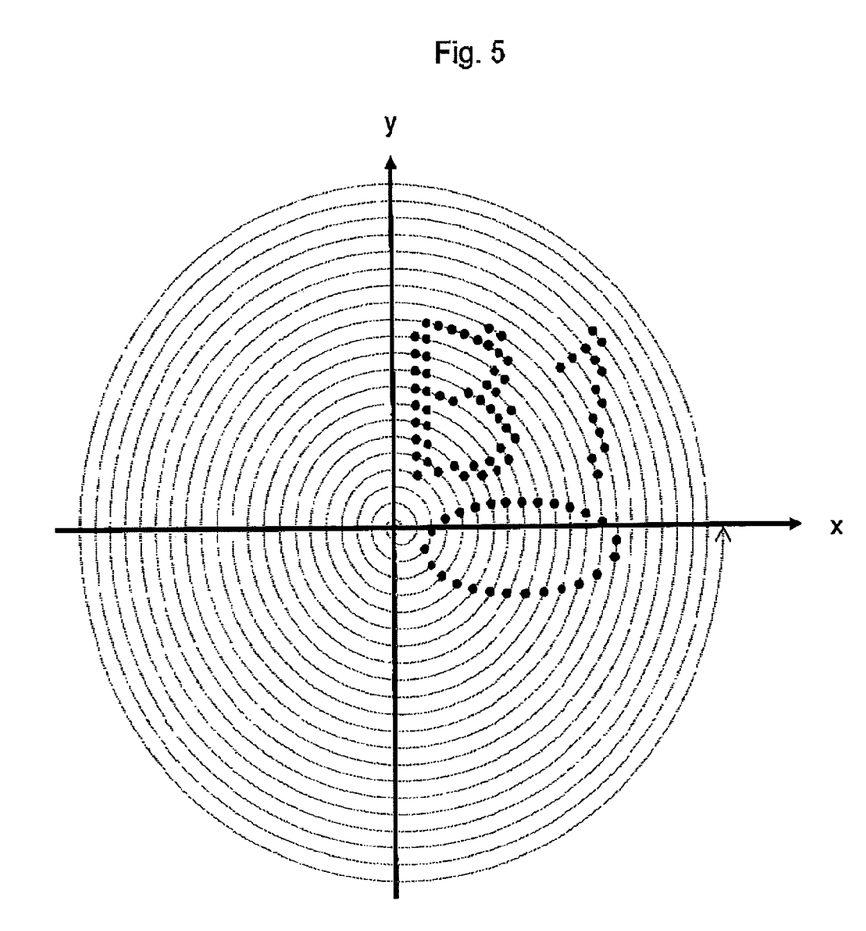
FIG. 5 shows the arrangement order of the first data array before the spiral-raster scan conversion, and gives an example of drawing by marking.

Thus, white light is emitted to the surface of the tissue of the photographic subject, with white light drawing the spiral track on the surface of the tissue according to the movement of the tip 11a (see the dotted arrow in FIG. 5).

During the scan period, the emission timing of the fourth laser 33d of the light source 31 is controlled so as to draw drawing contents on a drawing position of the surface of the tissue. The drawing contents and the drawing position are manually set by the operator. Characters, figures, etc., are cited as drawing content examples.

Specifically, in drawing periods of the scan period, the fourth laser 33*d* emits. The drawing periods correspond to a drawing area that is determined on the basis of the drawing contents and the drawing position.

Thus, infrared light is emitted to the surface of the tissue of the photographic subject in the drawing periods, with infrared light drawing the characters or figures on the spiral track on the surface of the tissue according to the movement of the tip 11*a* (see the black circle points in FIG. 5).

In FIG. 5, the characters "B1" and the oval are drawn by the fourth laser 33*d*. For example, the oval is drawn so as to surround the area presumed to be the affected region, and the characters "B1" are drawn in the vicinity of the affected region in order to specify the position of the affected region.

The processor 30 has a light source 31, a driving unit 41 for scanning, a light sensor 51, a controller, a memory 64, a front panel 65, and an encoder (a video-signal generator) 67. The controller includes a timing controller 61, a system controller 62, and a signal processor 63.

The light source 31 supplies light to the fiber 11 of the probe 10. The light, which is supplied by the light source 31 to the fiber 11, includes illumination light from the first, second, and third lasers 33*a*, 33*b*, and 33*c*, and light for drawing by the fourth laser 33*d*.

The driving unit 41 supplies a control signal to the scan unit 13 of the probe 10.

The light sensor 51 receives the light from the fibers 15. In other words, it receives the reflected light and fluorescence from the photographic subject based on the light from the light source 31, with the light from the fibers 15 being separated into the three wavelength ranges. In addition, the light sensor 51 performs a photoelectric conversion of the incident light.

The processor 30 performs image processing on the image signal based on the light from the fibers 15 of the probe 10, in order to generate and output a video signal to be displayed on the display 90.

The light source 31 has a first driver 32*a*, a second driver 32*b*, a third driver 32*c*, a fourth driver 32*d*, a first laser 33*a*, a second laser 33*b*, a third laser 33*c*, a fourth laser 33*d*, an RGB combining unit 34, a combining unit 35, and a first condenser lens 36 for illuminating and drawing.

The first laser 33*a* is a red light laser diode, and emits light in a first wavelength range including a first wavelength $\lambda_R$ on the basis of the control of the timing controller 61, the system controller 62, and the first driver 32*a*. The first wavelength $\lambda_R$ is about 630 nm.

The second laser 32*b* is a green light laser. For example, the second laser 33*b* may consist of an infrared laser diode together with a wavelength conversion board, and emits light in a second wavelength range including a second wavelength $\lambda_G$ on the basis of the control of the timing controller 61, the system controller 62, and the second driver 32*b*. The second wavelength $\lambda_G$ is about 530 nm.

The third laser 33*c* is a blue laser diode, and emits light in a third wavelength range including a third wavelength $\lambda_B$ on the basis of the control of the timing controller 61, the system controller 62, and the third driver 32*c*. The third wavelength $\lambda_B$ is about 440 nm.

The three wavelength ranges are narrow wavelength ranges and do not overlap.

The first, second, and third lasers 33*a*, 33*b*, and 33*c* are used for illuminating. Emission of the first, second, and third lasers 33*a*, 33*b*, and 33*c* is performed in the scan periods (see (1) in FIG. 3).

Figure 3:
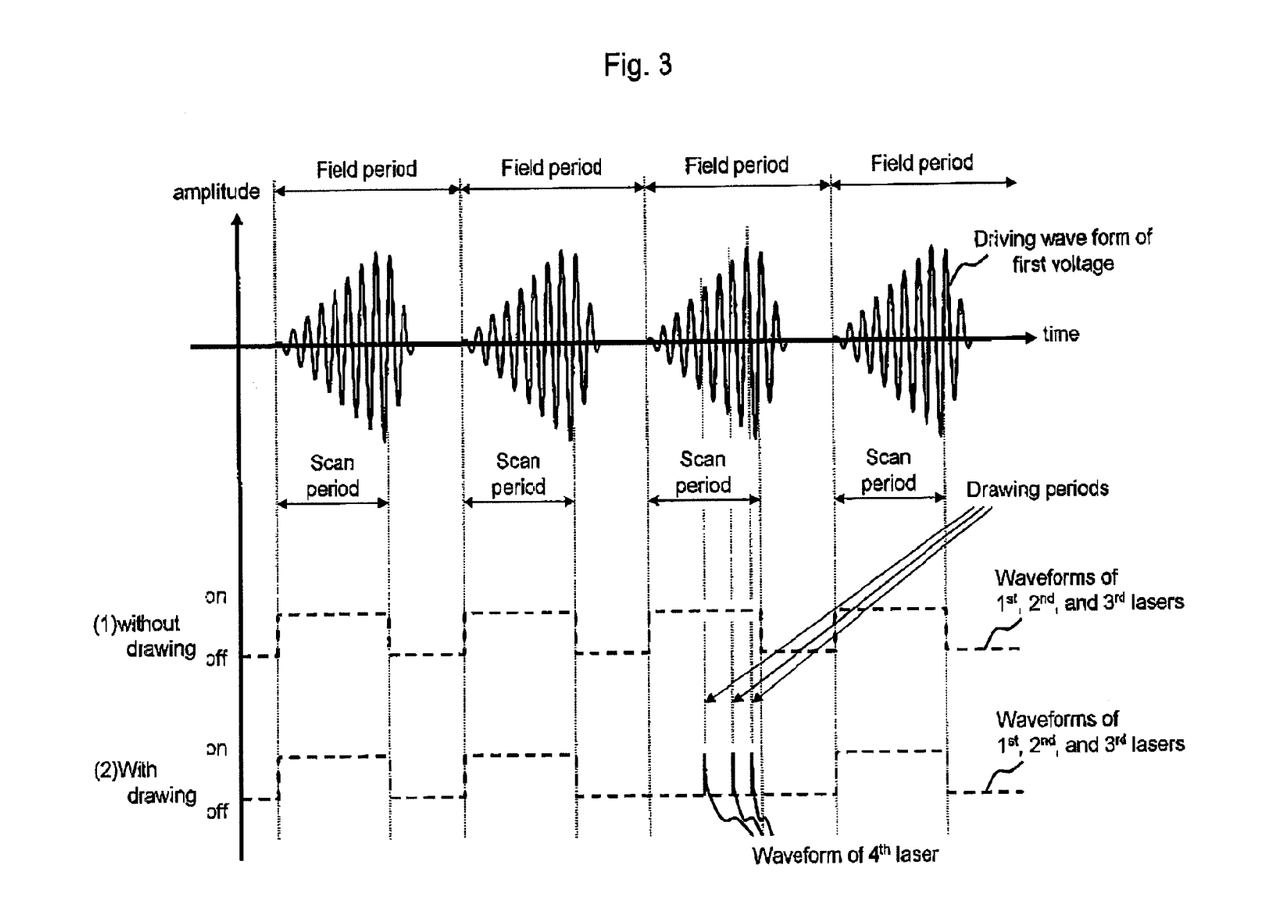
FIG. 3 is a timing chart that shows driving waveforms of the first voltage, and the first, second, third, and fourth lasers.

However, the first, second, and third lasers 33*a*, 33*b*, and 33*a* do not emit in the scan period including a period (the drawing periods) in which the fourth laser 33*d* emits (see (2) in FIG. 3).

In the embodiment, white light (illumination light) based on the RGB light by the first, second, and third lasers 33*a*, 33*b*, and 33*c* is used for illuminating the photographic subject. However, excitation light may be used for illuminating the photographic subject instead of white light.

The fourth laser 33*d* is an infrared laser diode, and emits infrared light in a fourth wavelength range including a fourth wavelength $\lambda_{SEM}$ or a fifth wavelength range including a fifth wavelength $\lambda_{TAG}$ on the basis of the control of the timing controller 61, the system controller 62, and the fourth driver 32*d*.

The fourth wavelength $\lambda_{SEM}$ ranges from about 655 nm to 980 nm. The fifth wavelength $\lambda_{TAG}$ is about 1065 nm.

The fourth laser 33*d* is the semiconductor laser that emits infrared light in the fourth wavelength range, or the YAG (Yttrium Aluminum Garnet) laser that emits infrared light in the fifth wavelength range.

The fourth laser 33*d* is used for drawing. Emission of the fourth laser 33*d* is performed in the drawing periods of the scan period following a drawing command resulting from operation of the front panel 65 or operation of the foot switch (not depicted).

Emission intensity of the fourth laser 33*d* is stronger than that of the first, second, and third lasers 33*a*, 33*b*, and 33*c*.

Emission of the infrared light having the comparatively strong emission intensity, applies heat to the part that receives the infrared light, thereby marking it.

After the scan period in which the fourth laser 33*d* emits infrared light, the photographic subject on which the marking has been performed can be imaged.

Figure 8:
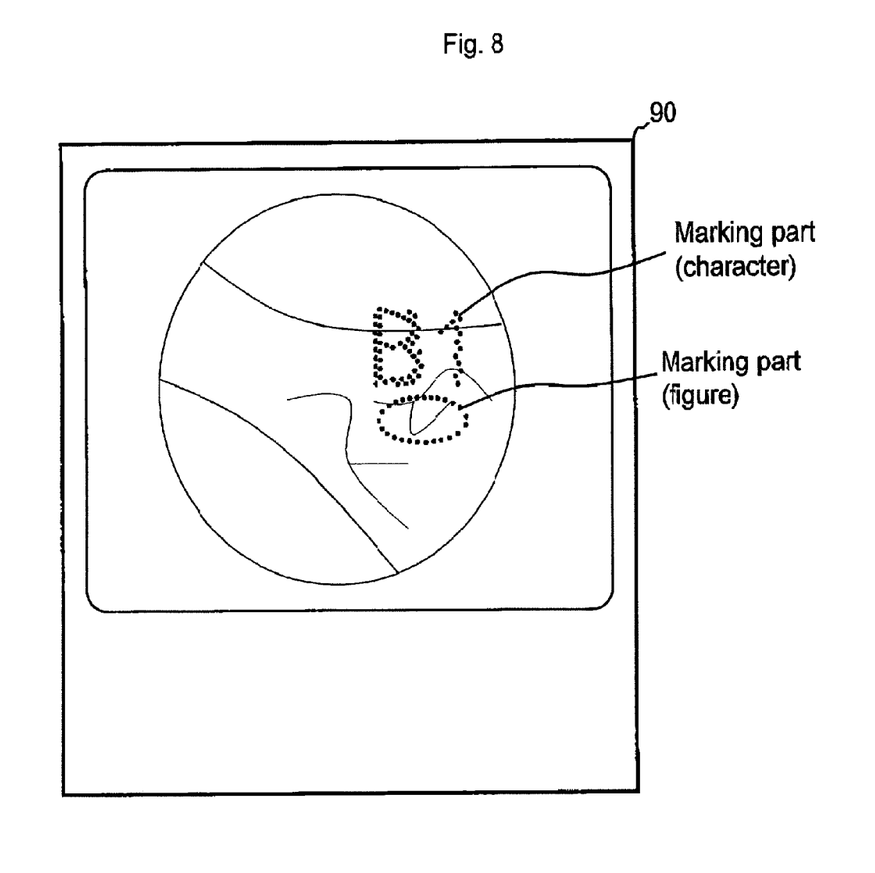
FIG. 8 is the display that displays the photographic subject after marking.

The display 90 in FIGS. 1 and 8 shows that the photographic subject image is displayed with characters "B1" and an oval drawn on the photographic subject.

While the operator observes the photographic subject image on the display 90, the operator operates an input apparatus in order to set the drawing contents and drawing position for marking.

An operation key of the front panel 65, and a touch panel set on the display part of the display 90 on which the photographic subject image is indicated, etc., are cited as input apparatuses.

In particular, when the touch panel is used as the input apparatus, the drawing contents and the drawing position can be set by touching a predetermined part on the photographic subject image on the display 90 so that the operation can be visually simplified.

When the drawing contents and position are set, bitmap data corresponding to the drawing contents and position is generated. The data array of the bitmap data is remapped to a data array corresponding to the spiral track scanning by the signal processor 63 (i.e., raster scan-spiral conversion). The remapped data is temporarily stored in the memory 64.

The data, which is remapped to the data array corresponding to the spiral track scanning, is read out from the memory 64 according to the drawing command, and is used for generating the timing pulse that controls the drawing periods in which the fourth laser 33*d* emits.

In the embodiment, the drawing contents, which are characters and figures, are manually set by the operator, however, the drawing contents may be automatically set by the system controller 62, etc. Specifically, the system controller 62 may automatically set numbers in order as the drawing contents. In this case, the time required to set the drawing contents can be reduced.

Furthermore, in the embodiment, the drawing position is manually set by the operator, however, the drawing position may be automatically calculated on the basis of the luminance or chroma of the image signal obtained by the emission of the first, second, and third lasers 33a, 33b, and 33c, in the previous scan period before the scan period including the period (the drawing periods) in which the fourth laser 33d emits.

For example, the image signal may be converted to the binary image on the basis of a luminance or chroma threshold. The binary image has a first area whose luminance or chroma is greater than the threshold and a second area whose luminance or chroma is not greater than the threshold. One of the first area, the second area, the vicinity of the first area, and the vicinity of the second area is selected as the drawing position.

In particular, in the case that excitation light is emitted to the photographic subject instead of white light based on the RGB light from the first, second, and third lasers 33a, 33b, and 33c, the region of weak autofluorescence in the photographic subject image is assumed to be the affected region, so that the faint region of autofluorescence, in other words, a low luminance region, or its vicinity, can be determined as the drawing position.

The light paths of the first, second, and third lasers 33a, 33b, and 33c are combined into one by the RGB combining unit 34.

The light paths of the fourth laser 33d and the RGB combining unit 34 are combined into one by the combining unit 35.

The resulting white light from the RGB combining unit 34 is condensed by the first condenser lens 36 and is transmitted to the fiber 11.

The infrared light from the fourth laser 33d is also condensed by the first condenser lens 36 and is transmitted to the fiber 11.

The driving unit 41 for scanning has a first DA converter 42a, a second DA converter 42b, a first scan driver 43a, and a second scan driver 43b.

The first DA converter 42a converts a timing pulse output from the timing controller 61 to an analog signal. On the basis of the analog signal converted by the first DA converter 42a, the first scan driver 43a drives the scan unit 13 such that the tip 11a of the fiber 11 oscillates in direction x.

The second DA converter 42b converts a timing pulse output from the timing controller 61 to an analog signal. On the basis of the analog signal converted by the second DA converter 42b, the second scan driver 43b drives the scan unit 13 such that the tip 11a of the fiber 11 oscillates in direction y.

The first scan driver 43a applies a first voltage on a first electrode of the scan unit 13 for driving in direction x. The first voltage has a sinusoidal waveform which is amplified at a predetermined rate for each scan period (about 25 msec; see FIG. 3).

The second scan driver 43b applies a second voltage on a second electrode of the scan unit 13 for driving in direction y. The second voltage has a sinusoidal waveform with the same shape as that of the first voltage and has a phase lag of $\pi/2$ with respect to the first voltage.

The light sensor 51 has a second condenser lens 52 for receiving, a first separation mirror 53a, a second separation mirror 53b, a first mirror 54a, a second mirror 54b, a first light-sensitive element 55a, a second light-sensitive element 55b, a third light-sensitive element 55c, a first AD converter 56a, a second AD converter 56b, and a third AD converter 56c.

The first separation mirror 53a and the second separation mirror 53b separate light of a predetermined wavelength range, as a dichroic mirror would.

Figure 4:
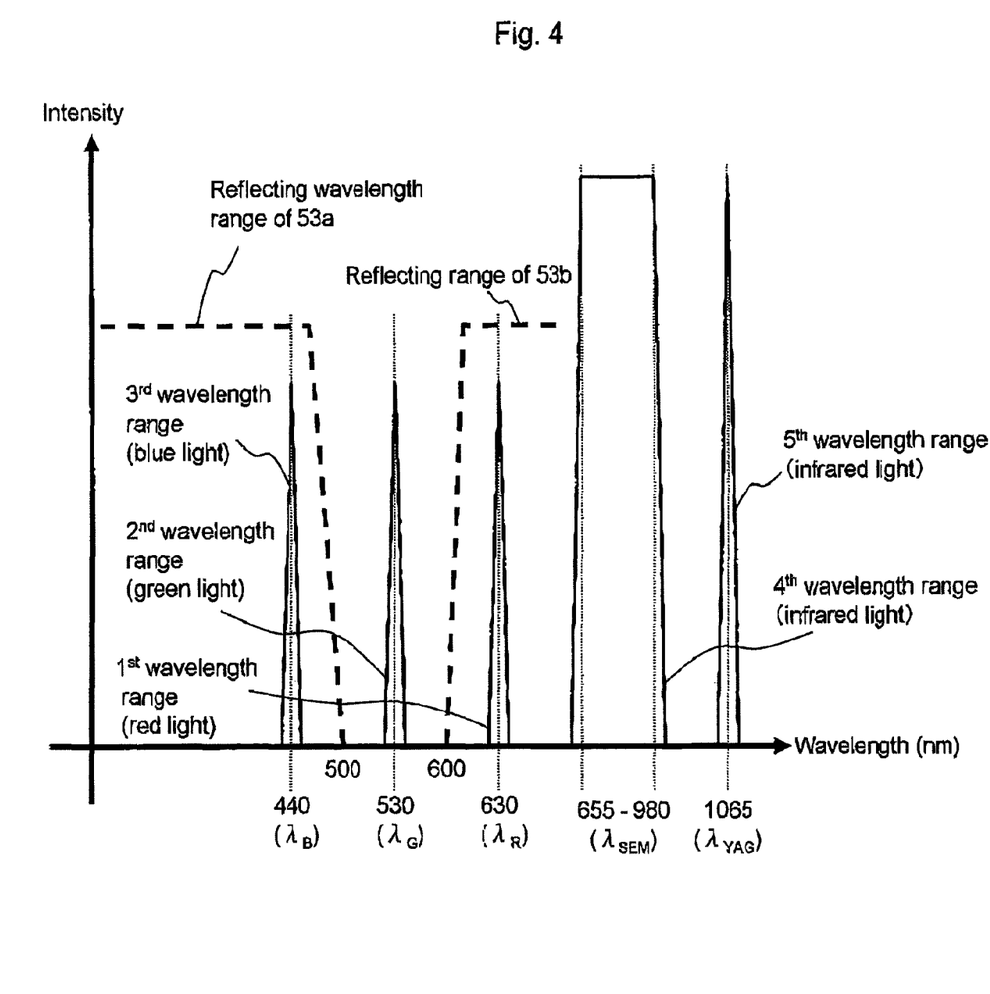
FIG. 4 shows the wavelength ranges of the light output from the first, second, third, and fourth lasers.

Short-wavelength light (i.e., blue light of less than 500 nm), in other words, the blue light including the third wavelength range, is reelected by the first separation mirror 53a (see FIG. 4).

The other lights, in other words, the red light including the first wavelength range and the green light including the second wavelength range, pass through the first separation mirror 53a.

Long-wavelength light (i.e., red light of more than 600 nm), in other words, the red light including the first wavelength range, is reflected by the second separation mirror 53b.

The remaining light, in other words, the green light including the second wavelength range, passes through the second separation mirror 53b.

The first light-sensitive element 55a, the second light-sensitive element 55b, and the third light-sensitive element 55c consist of a photodetector such as photomultiplier tube, etc.

The light transmitted from the fibers 15 is converted to a parallel light beam by the second condenser lens 52.

Then, the red light in the parallel light boom reaches the first light-sensitive element 55a through the first separation mirror 53a, the second separation mirror 53b, and the first mirror 54a.

The green light in the parallel light beam reaches the second light-sensitive element 55b through the first separation mirror 53a and the second separation mirror 53b.

The blue light in the parallel light seam reaches the third light-sensitive element 55c through the first separation mirror 53a and the second mirror 54b.

The first light-sensitive element 55a performs the photoelectric conversion on the rod light incident on the first light-sensitive element 55a.

The first AD converter 56a performs the AD conversion on the red light incident on the first light-sensitive element 55a after the photoelectric conversion, and then outputs the analog signal of the red light to the signal processor 63.

The second light-sensitive element 55b performs the photoelectric conversion on the green light incident on the second light-sensitive element 55b.

The second AD converter 56b performs the AD conversion on the green light incident on the second light-sensitive element 55b after the photoelectric conversion, and then outputs the analog signal regarding the green light to the signal processor 63.

The third light-sensitive element 55c performs the photoelectric conversion on the blue light incident on the third light-sensitive element 55c.

The third AD converter 56c performs the AD conversion on the blue light incident on the third light-sensitive element 55c after the photoelectric conversion, and then outputs the analog signal regarding the blue light to the signal processor 63.

The controller, which includes the timing controller 61, the system controller 62, and the signal processor 63, controls emission timing of a first emitter including the first, second, and third lasers 33a, 33b, and 33c and a second emitter including the fourth laser 33d.

Based on control of the emission timing, the fourth laser 23d emits in the drawing periods of one of the scan periods so as to shine infrared light on at least one part of the photographic subject, in order to mark.

Next, the details of the controller are explained.

The timing controller 61 supplies a timing pulse to all parts of the processor 30, based on control by the system controller 62, so as to control the operation of all parts of the processor 30.

In particular, the timing controller 61 supplies the timing pulse, which controls the drawing periods in which the fourth laser 33d emits, on the basis of the drawing contents and drawing position that are set by the operation of the front panel 65, to the fourth driver 32d.

Figure 6:
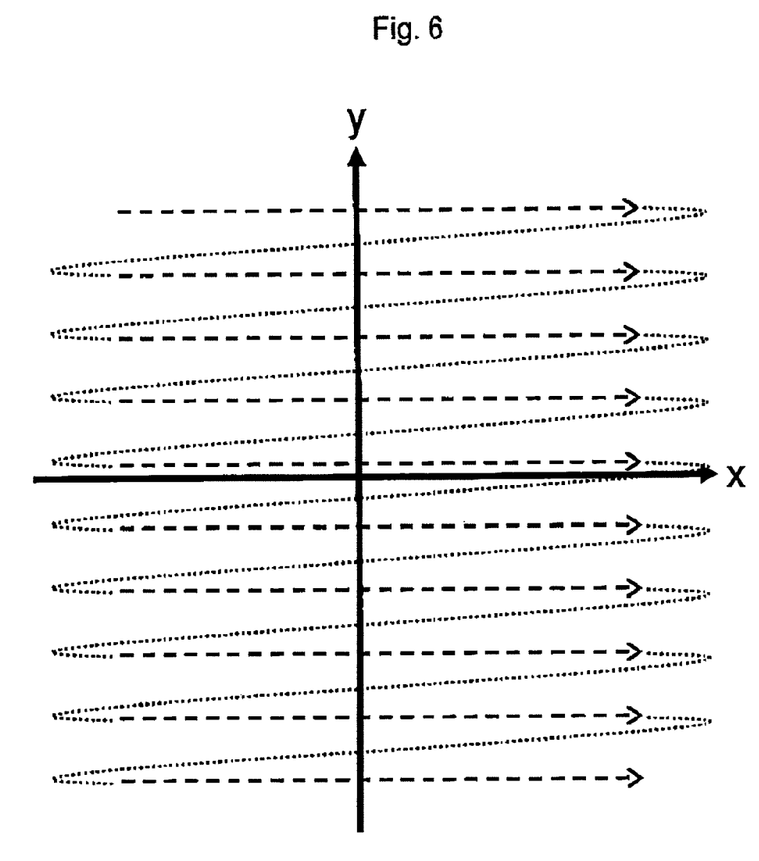
FIG. 6 shows the arrangement order of the second data array after the spiral-raster scan conversion.

The signal processor 63 performs a remapping from a first data array of the image signal obtained by the spiral track scanning, in other words, the first data array of the image signal of the reflected light that is arranged in the spiral-shaped trace of illumination (see FIG. 5), to a second data array ordered in x-y coordinates (i.e., the spiral-raster scan conversion, see FIG. 6).

Then, the signal processor 63 performs primary image processing on the image signal whose data array is rearranged from the first data array to the second data array, such as gamma correction, edge enhancement, etc.

However, the signal processor 63 does not perform the primary image processing on the image signal obtained in the scan period when the fourth laser 33d emits.

After the primary image processing, the image signal is temporarily stored in the memory 64.

The image signal, which is temporarily stored in the memory 64, is output to the encoder 67, in the predetermined is timing.

Figure 7:
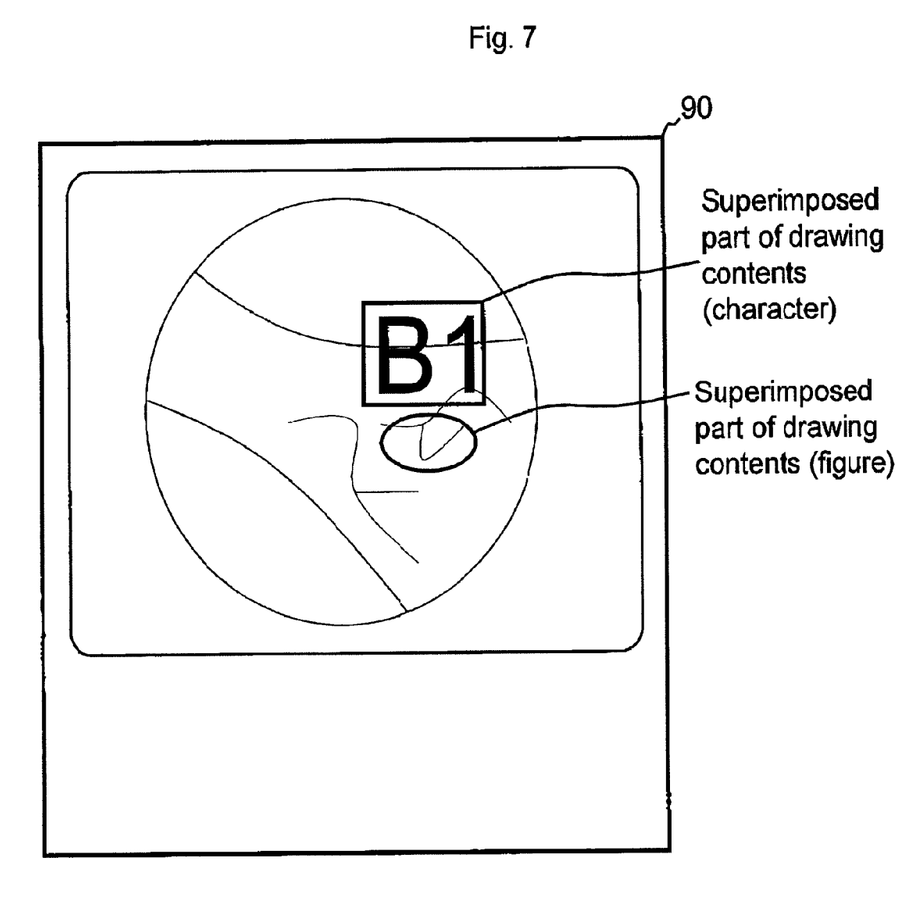
FIG. 7 is the display that superimposes the drawing contents on the photographic subject image.

Furthermore, the signal processor 63 outputs a superimpose signal to the encoder 67 so as to superimpose the drawing contents at the drawing position on the photographic subject image on the display 90, with the superimpose signal being layered on the image signal temporarily stored in the memory 64, in order to confirm the drawing contents and drawing position (see FIG. 7).

The drawing contents are superimposed on the photographic subject image on the display 90, from when the drawing contents are set by the operator, to when the drawing contents are drawn on the photographic subject.

FIG. 7 shows that the drawing contents are superimposed at the drawing position on the photographic subject image on the display 90 before marking.

After the fourth laser 33d emits in response to the drawing command, the drawing contents are drawn at the drawing position on the photographic subject so that the above described superimposition is not performed.

FIG. 8 shows that the fourth laser 33d emits in the drawing periods of the scan period so that the drawing contents are drawn on the photographic subject. The first, second, and third lasers 33a, 33b, and 33c fire on the photographic subject in the scan period after emission of the fourth laser 33d, and the photographic subject image based on emission of the first, second, and third lasers 33a, 33b, and 33a is displayed on the display 90.

Furthermore, the signal processor 63 specifies the drawing area in the image signal after primary image processing where the drawing contents are drawn on the basis of the drawing contents and drawing position that are set by the operator.

Then the signal processor 63 converts the luminance information of a predetermined area including the drawing area to binary data, and determines whether the binary data is less than or equal to the threshold.

If the binary data is less than or equal to the threshold, the signal processor 63 determines that it is not appropriate to assume the predetermined area as an affected region because the distance between the predetermined area and the tip 11a is so great that the luminance of the predetermined area is dark. Then, the signal processor 63 cancels the drawing by the fourth laser 33d and gives a warning on the display 90 (see FIG. 9).

Figure 9:
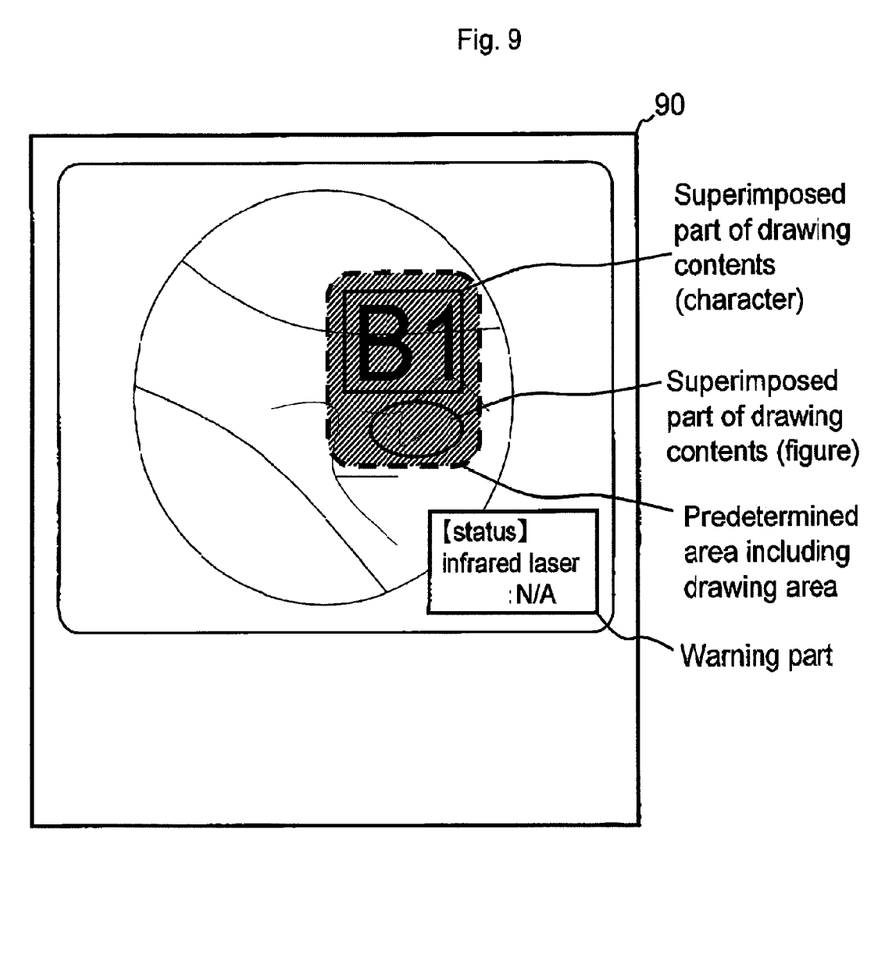
FIG. 9 is the display that superimposes a warning on the photographic subject image.

Specifically, the signal processor 63 outputs a warning signal on the photographic subject image on the display 90 to the encoder 67, with the warning signal being layered on the image signal temporarily stored in the memory 64.

FIG. 9 shows that the drawing command is issued to draw characters "B1" and an oval at the drawing position in the vicinity of the area which is assumed to be affected. But, the predetermined area is too dark, it is difficult to determine whether this area is affected or not. In other words, it is possible that the color of this area is different from the surrounding area because it is affected, or merely because of insufficient illumination. So, in this case, a warning of the cancellation of drawing is given, and the area is highlighted (as in the area surrounded by the broken line).

The encoder 67 performs secondary image processing on the image signal from the signal processor 63, so as to generate the video signal (the luminance signal and the color-difference signal) for displaying on the display 90, and then outputs the video signal to the display 90.

In the embodiment, marking of the intended part of the photographic subject is performed by shining of the fourth laser 33d through the fiber 11.

Therefore, marking can be performed easily and accurately compared to an embodiment in which marking is performed by a treatment device. In order to mark, a treatment device must be brought near a target in the vicinity of the affected region through the forceps channel.

Furthermore, the intended drawing contents, such as characters, figures, etc., can be drawn on the intended drawing position that is at least one part of the photographic subject, by emission from the tip 11a of the fiber 11 in predetermined periods (drawing period) with the tip 11a of the fiber 11 being moved in a spiral as viewed from the direction z.

Therefore, the marked part can be easily confirmed after marking, as compared to an embodiment in which only a simple figure such as a dot drawn.

In the embodiment, in the scan period including the drawing periods in which the fourth laser 33d emits in order to mark with infrared light, emission of the first, second, and third lasers 33a, 33b, and 33c is stopped, and primary image processing on the image signal obtained in the field period including this scan period (the drawing periods) is not performed.

However, even in this scars period, the first, second, and third lasers 33a, 33b, and 33c fire and primary image processing on this image signal may be performed, with an infrared cut filter being arranged between the second condenser lens 52 and the first, second, and third lasers 55a, 55b, and 55c.

Moreover, in the embodiment, infrared light emitted from the fourth laser 33d in shone on the photographic subject for marking through the fiber 11.

However, infrared light may be shone on the photographic subject for a different treatment such as PDT (Photo Dynamic Therapy), etc.

Although the embodiments of the present invention have been described herein with reference to the accompanying drawings, obviously many modifications and changes may be made by those skilled in this art without departing from the scope of the invention.

The present disclosure relates to subject matter contained in Japanese Patent Application No. 2008-092651 (filed on Mar. 31, 2008) which is expressly incorporated herein by reference, in its entirety.

The invention claimed is:

1. An endoscope system comprising:
a first emitter that emits at least one of illumination light and excitation light to a photographic subject;
a second emitter that emits infrared light, emission intensity or said second emitter being stronger than emission intensity of said first emitter;
a fiber that has a tip which moves in a spiral when viewed from said photographic subject during scan periods; and
a controller that controls emission timing of said first emitter and said second emitter;
light emitted by said first emitter and said second emitter being cast from said tip of said fiber onto said photographic subject;
said second emitter emitting in a predetermined period of one of said scan periods, based on control of said emission timing, so as to shine infrared light with said second emitter to at least one part of said photographic subject, in order to perform marking.

2. The endoscope system according to claim 1 wherein said controller calculates said predetermined period on the basis of a drawing position and drawing contents for said marking, said drawing contents being drawn at said drawing position of said photographic subject by said emission of said second emitter.

3. The endoscope system according to claim 2, wherein said controller calculates said drawing position on the basis of the luminance or chroma of the image signal obtained by emission of said first emitter in a previous scan period of said scan periods, before the scan period including said predetermined period in which said second emitter emits.

4. The endoscope system according to claim 2, further comprising an input apparatus in order to set said drawing contents and said drawing position.

5. The endoscope system according to claim 1, wherein said controller determines whether said second emitter emits, on the basis of the luminance of a predetermined area in the image signal obtained by emission of said first emitter in a previous scan period of said scan periods, before a scan period including said predetermined period in which said second emitter omits; said predetermined area including a drawing area on which infrared light from said second emitter is shone.

6. An endoscope system comprising:
a first emitter that emits at least one of illumination light and excitation light to a photographic subject;
a second emitter that emits infrared light, emission intensity of said second emitter being stronger than emission intensity of said first emitter;
a fiber that has a tip which moves in a spiral when viewed from said photographic subject during scan periods; and
a controller that controls emission timing of said first emitter and said second emitter;
light emitted by said first emitter and said second emitter being cast from said tip of said fiber onto said photographic subject;
said second emitter emitting in a predetermined period of one of said scan periods, based on control of said emission timing, so as to shine infrared light with said second emitter to at least one part of said photographic subject.

* * * * *